United States Patent [19]

Berger et al.

[11] Patent Number: 4,896,097
[45] Date of Patent: Jan. 23, 1990

[54] APPARATUS FOR THE EXAMINATION OF MEASURING GASES BY MEANS OF MICROWAVES

[75] Inventors: Lutz Berger, Eggenstein; Gunther Krieg, Karlsruhe; Johann Pappert, Weingarten; Gerhard Schmitt, Karlsruhe, all of Fed. Rep. of Germany

[73] Assignee: Kernforschungszentrum Karlsruhe GmbH, Karlsruhe, Fed. Rep. of Germany

[21] Appl. No.: 71,655

[22] Filed: Jul. 9, 1987

[30] Foreign Application Priority Data

Jul. 9, 1986 [DE] Fed. Rep. of Germany ....... 3622956

[51] Int. Cl.[4] .......................................... G01N 22/00
[52] U.S. Cl. ....................................... 324/639; 73/23; 324/636
[58] Field of Search ................ 324/58 A, 58 R, 58 C, 324/58.5 A, 58.5 R, 58.5 C; 73/23

[56] References Cited

U.S. PATENT DOCUMENTS

| | | | |
|---|---|---|---|
| 2,824,280 | 2/1958 | Beers | 324/58.5 A |
| 2,982,855 | 5/1961 | Wickersham | 324/58.5 A |
| 3,031,616 | 4/1962 | Hummel | 324/58 A |
| 3,443,217 | 5/1969 | Brinkerhoff | 324/58.5 A |
| 3,456,187 | 7/1969 | Akao et al. | 324/58.5 C |
| 3,691,454 | 9/1972 | Hrubesh et al. | 324/58.5 C X |
| 3,866,118 | 2/1975 | Ghosh et al. | 324/58.5 A |
| 3,889,182 | 6/1975 | Easley et al. | 324/58.5 A |
| 3,973,186 | 8/1976 | Uehara et al. | 324/58.5 A |

*Primary Examiner*—Reinhard J. Eisenzopf
*Assistant Examiner*—Robert W. Mueller
*Attorney, Agent, or Firm*—Spencer & Frank

[57] ABSTRACT

An apparatus for the analysis of gaseous media, the apparatus composed of a microwave transmitter; a microwave receiver; a measuring cell disposed between the transmitter and the receiver, composed of at least one Stark chamber, and having a gas inlet and a gas outlet; at least one Stark electrode disposed in, and electrically insulated from, the chamber; and a plurality of mutually spaced holders holding the electrode in a predetermined position in the chamber.

28 Claims, 6 Drawing Sheets

APPARATUS FOR THE EXAMINATION OF MEASURING GASES BY MEANS OF MICROWAVES

BACKGROUND OF THE INVENTION

The present invention relates to an apparatus for the analysis of gaseous media, the apparatus including at least one microwave transmitter, at least one measuring cell having at least one gas inlet and one gas outlet, a detector and at least one high voltage Stark electrode disposed in the measuring cell and insulated therefrom.

It is known to analyze gaseous media, possibly also after conversion of a solid substance or a liquid into the gaseous state, by absorption of microwaves within certain characteristic frequency ranges by the excitation of rotational transitions in molecules of the media to be examined. In order to reduce the spectroscopic line width, the examination takes place in the low pressure range.

The absorption lines are split by utilizing the Stark effect, an alternating Stark voltage preferably being applied to increase detection sensitivity. Such a process is highly selective in principle but does not require prior changes, such as ionization or chemical reactions of the substances to be examined.

In the prior art devices, the measuring cells are overdimensioned. Moreover, extensive memory effects have been noted. These effects are manifested in that a once measured gas can still be detected even after a certain time has elapsed. The overdimensioning of the absorption cell is required, in particular, because the high voltage Stark electrodes or the Stark septum can be inserted only into cells having an overdimensioned cross section. Moreover, the Stark septum employs carrier materials, such as Teflon, which may also absorb gases, which likewise results in increased memory effects. The gas intake and outlet are also of a disadvantageous configuration; they have considerable dead space, which likewise increases the memory effects.

SUMMARY OF THE INVENTION

It is an object of the present invention to provide an apparatus of the above-mentioned type which avoids the stated drawbacks.

This is accomplished, according to the present invention, with an apparatus for the analysis of gaseous media, the apparatus including at least one microwave transmitter, at least one measuring cell having at least one gas inlet and one gas outlet, a detector, and at least one high voltage Stark electrode disposed in the measuring cell and insulated therefrom, in that the Stark electrode is held in the cell by means of a plurality of spaced holders.

In this way, the possibilities of accumulation of gases in the cell are reduced considerably. Preferably, the holder is made of a ceramic material, preferably a glass ceramic material. A material known by the tradename "Vestel" may also be used.

While in the prior art, as explained, a Teflon band is employed as the carrier for the Stark septum, to which the high voltage Stark electrodes are applied, and this band is placed and glued onto a side wall, for example the bottom of the cell, the present invention preferably provides ceramic carriers which, in contrast to Teflon, do not support the accumulation of gases, particularly if the carriers are of a glass ceramic material. The use of insulating carriers of a glass ceramic material additionally permits the use of the apparatus according to the invention at substantially higher temperatures, such as, for example, at 250° C. In particular, a plurality of spaced individual holders may be provided in the cell to hold the Stark electrode. Preferably the height of the holders corresponds to the internal height of the cell, with the holders being basically configured as small plates and being provided, at half their height, with at least one horizontal slit to accommodate an edge of the high voltage Stark electrode. In contrast to the cited prior art, the Stark electrode of this configuration is held in the center of the cell so that Stark fields are able to form from there in both directions, which results in homogenization of the field in the cell. In order to prevent the individual spacer members from shifting relative to the Stark electrode, a further feature provides that the edges of the Stark electrodes are equipped with recesses into each of which engages a projection on the holder.

The above mentioned configurations provide, in particular, a possibility for a further feature of the invention, according to which the cross section of the cells is adapted to the microwave frequency employed, i.e. is not overdimensioned, with the cell cross section being, in particular, <10 mm×5 mm and primarily the cell cross section being about 7×3.5 mm, preferably 7.1×3.6 mm. With this configuration, it is accomplished that transmitter, receiver, attenuator and possibly a waveguide switch as well as the reference and measuring cells all of the same waveguide cross section so that no cross-sectional transitions with tapers or the like are required, as this is the case in the prior art. With a Stark modulation, the selected small cell cross sections result in the rotational transitions, being modulated out better and thus the detection sensitivity is increased.

According to a further highly advantageous feature, the measuring cell follows a meander pattern composed of arcuate sections and straight measuring sections, the latter constituting Stark chambers. Because of the meander shaped configuration, any desired number of arcuate sections and straight sections may be arranged one behind the other, contrary to other configurations, to attain optimum adaptation with nevertheless a compact structure. It is thus possible, without any loss of signal intensity, to realize a mechanical structure which fits into a so-called 19-inch rack.

If gas is supplied to measuring and reference cells, the problem arises that, on the one hand, the openings for introducing the gas into the waveguide should have a limited cross section so as not to interfere with the microwaves and, on the other hand, they should be sufficiently large to permit rapid gas exchange when the type of gas is changed so that response times remain low and thus a plurality of measurements can be made within a limited period of time. Moreover the gas should be supplied in a simple and inexpensive manner.

To solve the above problems the invention provides that, in two opposed side walls, the gas inlet and/or the gas outlet are provided with slits which are disposed opposite one another and are parallel to the longitudinal axis of the part containing the inlet or outlet, with such slits, in particular, having a length of about 10 mm and a width of about 0.5 mm. In this way, it is accomplished that the microwaves are practically not interfered with at all and nevertheless the measuring gas can be exchanged with sufficient speed through the slit-like configuration of the slits and the arrangement of the slits in pairs. To supply the gas to the slits or conduct it away from them, respectively, a further feature provides that a chamber extends around the side walls of the part containing the slits, in the region of the slits, and a gas intake/outlet is connected to such chamber.

The speed with which the measuring gas is exchanged is enhanced further in that an inlet valve is provided which has an inlet and an outlet as well as a flow path disposed between the two, with a branch for a measuring cell unit branching off therefrom at a finite angle, preferably at 90°. Such a valve may be controlled either mechanically or electrically. The measuring gas is here conducted at high speed past the intersection created by the above-described structure, between the high pressure region on the measuring gas side and the low pressure region in the waveguide or in the measuring cell. Only a small portion of the gas flowing by enters the measuring cell. Dead times as a result of dead volumes can thus also be substantially avoided.

Due to the above configuration, fluctuations in the pumping output of the vacuum system can be compensated for to an extent sufficient for the measuring cell.

If the microwave frequency is stabilized by the use of a reference cell which operates, in particular, with the zero passage of a reference signal generated by a reduced Stark voltage, with the zero passage being a function of the measurement of the actual zero absorption line and the Stark component with a phase shift about 180° obtained y means of a lock-in technique, it will be necessary to provide for further pressure stabilization.

Under the same conditions as stated above, namely that a reference cell is provided, a highly preferred embodiment has the reference cell connected in series with the measuring cell. Generally, when seen from the transmitter, the reference cell is then disposed in front of the measuring cell so that the useful signals are not reduced. This measure also enhances the compact structure of the entire device, facilitates thermostatization of the cells, eliminates the use of expensive directional couplers, and avoids separation of the signal into two branches, which separation would result in weakening of the signal. The measure further permits the detection of reference and measuring signals with one detector and preferably also further processing by means of a peramplifier if the reference and measurement signal are likewise given a difference in phase by means of phase shifted Stark voltages. The use of a preamplifier eliminates drift problems in particular, as well as problems resulting from a phase shift between two amplifiers.

If a plurality of absorption frequencies are to be examined, it may be provided that a plurality of microwave transmitters at different frequencies are associated with one measuring cell in which case exchange of the pure gas generator, for example a permeation systems, in the reference cell is avoided in that, according to a further feature, a plurality of reference cells are associated with one measuring cell, with the reference cells being connected either in series or in parallel with one another.

With such multi-component system, the microwave transmitters, which preferably include Gunn oscillators, must be connected via appropriate waveguide switches, either directly with the first reference cell or, via reference cells arranged in parallel, with the common measuring cell. The significant factor is that otherwise the entire arrangement remains the same, particularly also the electronic evaluation system including primarily a detector and a preamplifier and, together with the transmitters, only the Stark voltages in the measuring and reference cells need be switched.

The measurements of the various components are effected by actuation of the respective transmitter and applying the respective Stark voltages which, however, involves switching delays. Particularly for measurements of two components, two transmitters are thus preferred which may be connected with the measuring cell by way of switches, namely the reference cells in series, together with or in parallel with the measuring cell and the reference cells are charged with phase shifted Stark voltages while the transmitters are regulated separately. In contrast to the preceding solution, the above-mentioned frequency lock for both transmitters is possible which avoids time delays due to respectively renewed frequency synchronization.

Since it has been found that the above-mentioned zero passage of the microwave absorption signal is a function of pressure, pressure regulation is provided particularly for the reference measurement. A method according to the invention for pressure regulation is characterized in that the cell cross section is approximately $7 \times 3.5$ mm, preferably $7.1 \times 3.6$ mm.

The system according to the invention is particularly advantageous because, with subatmospheric pressure on both sides, a conventional pressure regulation by way of electrically controlled valves or the like is impossible. The pressure regulation method according to the invention is simple since it relies on a defined evaporation of the pure component to be measured. If the pressure drops due to fluctuations during extraction, i.e. by means of a pump, more intensive heating of the pure component causes it to evaporate more, so that the pressure is increased; if the pressure rises, the temperature is reduced or the system is cooled, so that the amount of evaporation is reduced and the overall pressure in the cell is reduced.

Preferably, the gas is extracted from the cell at a constant rate. With a constantly operating extraction pump, a constant flow is realized in that a capillary is disposed in the extraction path. It may also be provided that filters are connected downstream of the outlet and of the reference cell. Such a filter absorbs the component to be measured and prevents, in a vacuum system, the pure component from entering into the measuring cell to there possibly falsify the measuring result.

According to a preferred embodiment, the reference cell and measuring cell have a common thermostat system. This eliminates the requirement for thermal insulation between the reference cell and measuring cell.

Further advantages and features of the invention will become apparent from the description that follows in which significant features of the invention are described in detail with reference to the drawing figures.

DESCRIPTION OF THE PREFERRED EMBODIMENTS

Figure 1:
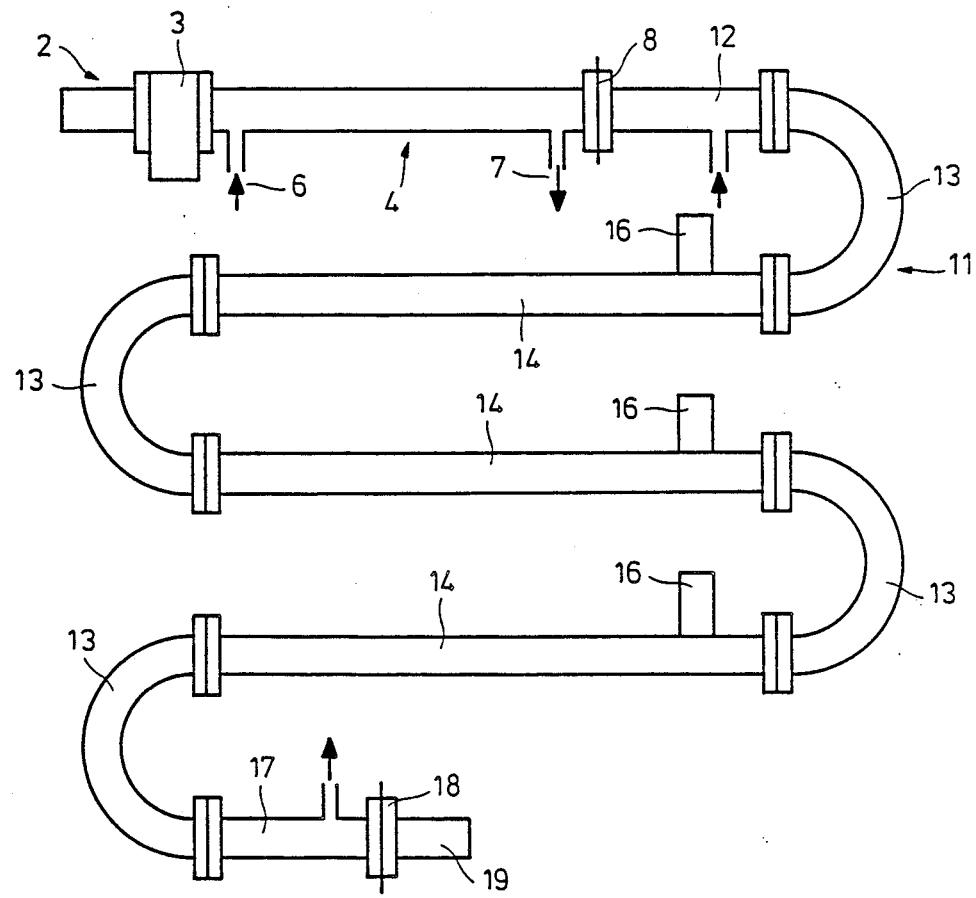
FIG. 1 is a basic pictorial view showing the layout of apparatus according to the invention.

FIG. 1 shows the basic overall physical arrangement of apparatus according to the invention or, more specifically, of a microwave process analyzer according to the invention.

This apparatus includes a microwave radiation transmitter 2, an isolator 3 disposed downstream thereof, and a reference cell 4 having a reference gas inlet 6 and an outlet 7. Reference cell 4 is followed by an insulating window 8, which is, in turn, followed by a measuring cell 11 having a gas inlet 12 in the region adjacent window 8. In order to avoid long structural lengths, measuring cell 11 is given a meander shape and is subdivided into a plurality of 180° arcs 13 and linear Stark chambers 14. In a conventional manner, Stark chambers 14 are provided with insulated Stark voltage leads 16. The spacer shown in FIG. 3 and as part 24 in FIG. 2 attaches the Stark electrode 21 exactly in the middle of the waveguide, electrically isolated to the walls. It's dimension h corresponds to the height of the inner waveguide dimension.

Finally measuring cell 11 has a gas outlet 17 followed by a detector 19 separated from cell 11 by a further insulating window 18.

Cells 4 and 11 constitute a waveguide and the cross section of measuring cell 11 and, in particular, of Stark chambers 14 is optimized for the respective microwave range in which the apparatus is to operate. In particular, if only one frequency is to be analyzed, the cross section is tuned to that frequency. The cross section is preferably 7.1 mm×3.6 mm, Preferably, microwave transmitter 2 includes a Gunn oscillator. If a plurality of gas components are to be analyzed, a plurality of transmitters may be connected, each via an appropriate waveguide switch, to common measuring/reference cells, with possibly one cell containing the components to be examined. The Stark voltages in the measuring and reference cell, respectively, are switched in to correspond to the active transmitters. In the case of a multicomponent gas system it may also be provided that, if the respective component is available for the reference cell in its pure form, a plurality of reference cells are connected mutually in parallel or all in series downstream of their associated transmitters and are switched in according to the respective measurement to be performed.

Figure 2:
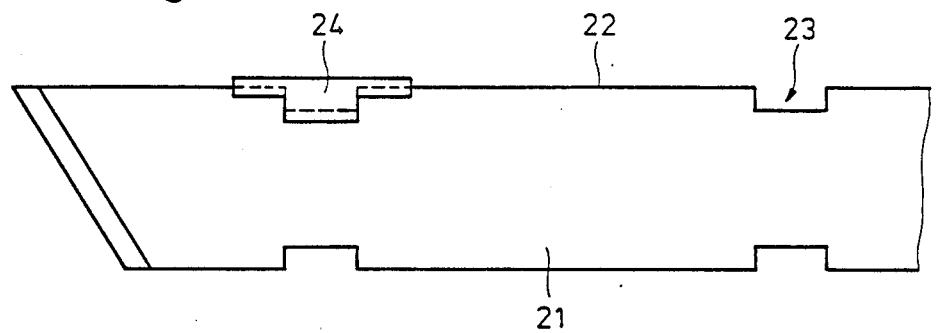
FIG. 2 is a top view of a Stark septum, employed in the apparatus of FIG. 1, with an insulating holder being provided at one location.
Figure 3:
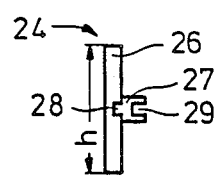
FIG. 3 is a side view of the insulating holder shown in FIG. 2.

A Stark septum and its holder are shown in FIGS. 2 and 3. The Stark septum 21 forming the internal conductor must be inserted in an insulated manner into the corresponding Stark chamber, which constitutes the external conductor. For this purpose, the longitudinal edges 22 of septum 21 are provided with recesses 23 in which engage insulated holders 24 preferably made of a glass ceramic. Recesses 23 fix the positions of septum 21 and insulated holders 24 with respect to one another in the longitudinal direction.

Insulated holders 24 have a height h corresponding to the height of the associated Stark chamber 14. Each holder 24 is composed of a plate 26 having a projection 27 at its center for engagement in a recess 23. Plate 26 and projection 27 are provided with respective slits 28, 29 lying in the same plane. After a holder 24 has been assembled to septum 21, slit 29 grips over the base of recess 23 and slit 28 grips over the edge 22 of the septum so that holder 24 is also fixed perpendicularly to the surface of septum 21. Septum 21 is inserted into the individual Stark chambers together with the attached holders 24.

Stark chamber 14 and septum 21 create the required Stark capacitance. The Stark voltage supply 16 has such a configuration that it has an external inductance which forms with the capacitance of Stark electrode 21 a parallel resonant circuit, with such external inductance, in turn, simultaneously serving as the high voltage coil of a transformer.

At the same time, the series connection of a capacitance, which has a much greater value than the capacitance off the Stark cells, in the resonant circuit and the incorporation of a diode with series resistance parallel to the Stark capacitance raises the d.c. level of the alternating Stark voltage in such a manner that the negative peak value of the alternating voltage is positioned at 0 volt.

Figure 4:
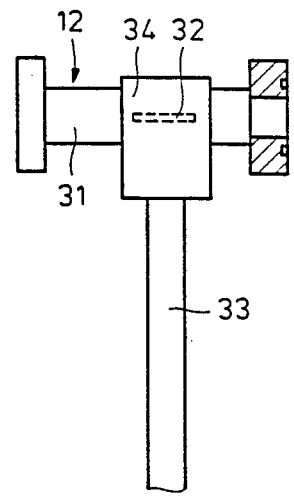
FIG. 4 is a detail view showing an inlet and outlet for gas into and out of a cell of the apparatus of FIG. 1.

One problem in such microwave analyzers is the uniform introduction of the gases, particularly the measuring gas, into the chambers and their removal in sufficient quantities in a short period of time so that a fast exchange of gases and short measuring periods result. For this purpose the present invention provides that each inlet or outlet 6, 7, 12, 17 is formed, as shown in FIG. 4, of two longitudinal slits 32 each provided in a respective one of two opposing side walls 31, slits 32 being directly opposite one another and being located along the center axes of side walls 31. Slits 32 communicate with a chamber 34 which surrounds the associated tube 4, 12, or 17 in the manner of a cuff and a conduit 33, which will be an inlet or an outlet conduit. It has been found that inlets and outlet equipped with two such slits permit high gas exchange speeds.

Figure 5:
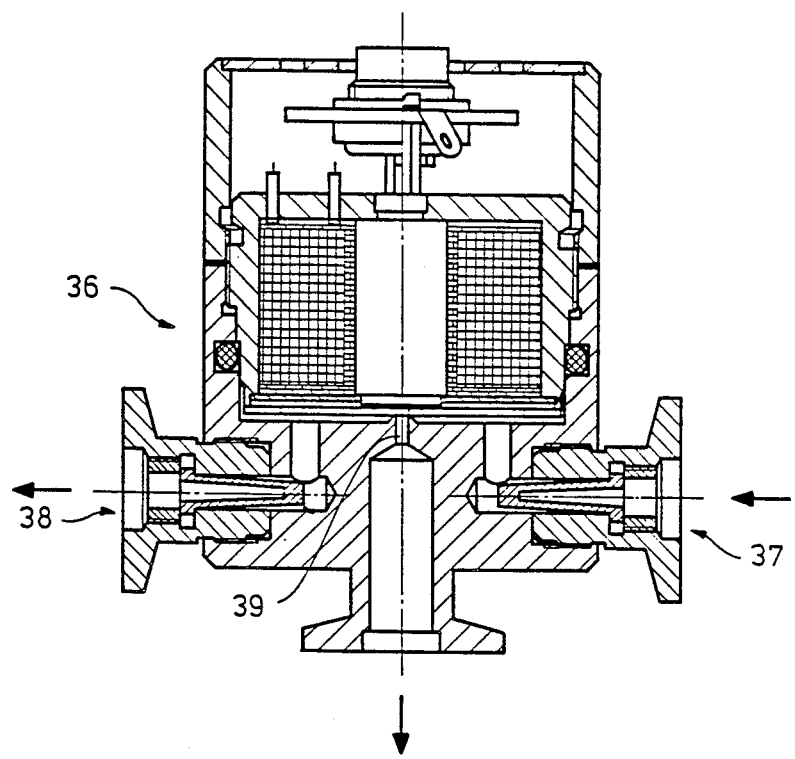
FIG. 5 is a cross-sectional view of a valve arrangement for supplying measuring gas to a measuring cell.

Conduit 33 associated with inlet 12 is further connected with a so-called cross valve 36, as shown in FIG. 5. In the valve, the gas to be supplied to the respective measuring chamber 14 is branched off via a side branch 39 by a valve which, when open, provides for the major path of gas flow to be from valve inlet 37 to the valve outlet 38. This reduces the amount of dead volume, because the sample to be analyzed is brought directly to the boundary between high pressure system connected to branch 37/38 and the vacuum system 39.

Figure 6:
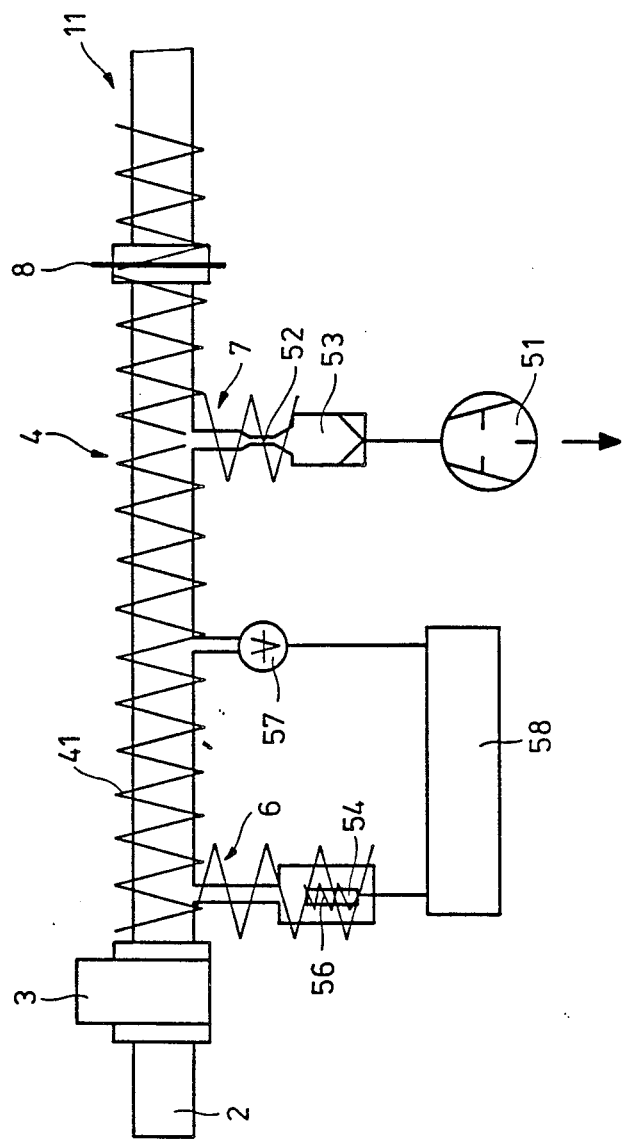
FIG. 6 is a simplified pictorial illustration of a pressure and temperature regulation arrangement.

FIG. 6 shows that reference cell 4 and measuring cell 11 are kept at the same temperature by a joint thermostat system 41. In this way, thermal insulation between the two systems is no longer necessary.

A constant pressure must be maintained particularly in reference cell 4. For that reason, the pressure regulation effected in measuring cell 11 by way of a regulating valve following up is not sufficient if there are fluctuations in the pump output of the vacuum system.

Initially a conventional vacuum pump 51 is connected to outlet 7 of reference cell 4. Outlet 7 has a capillary 52 which produces a constant gas flow. If only one vacuum system is employed, a filter 53 is connected downstream of capillary 52 to absorb the component to be measured and to thus prevent this component from reaching the measuring cell as a pure substance which would falsify the measurement. The samples to be analyzed in the measuring cell 11 flow from inlet 37 to the outlet 38 of the valve 36 passing the boundary to the vacuum system. A small amount of gas is pumped through 39 into the measuring cell 11.

The pure substance required for measuring the reference cell 4 is made available in a permeation vessel 54 containing it. Commerically made permeation tubes are attached to a Peltier element and placed into the vacuum chamber. This vessel is provided with a separate heating and/or cooling system 56 controlled in the following manner by means of a pressure regulating device 58 which is connected with a pressure sensor 57: if the suction output of the vacuum system 51 fluctuates, pressure fluctuations may occur in spite of the effect of capillary 52. These fluctuations are measured by pressure sensor 57 which, via pressure regulator 58 of permeation vessel 54, if the pressure drops, heats vessel 54 to increase permeation of the pure component and if the pressure increases, reduces the heating or cools vessel 54 to thus reduce the permeation output. This results in a precise and reliable pressure regulation.

A relatively good pressure constant is particularly necessary to regulate the microwave frequency and thus to stabilize it.

The frequency of the microwave transmitter and its Gunn oscillator are regulated and thus stabilized in the following manner: a further Stark voltage which is shifted in phase with respect to the Stark voltage supplied to measuring cell 11, preferably by 90°, is derived from the Stark voltage generator and fed to reference cell 4.

The actual intensity measurement is made at the maximum of the absorption line and, in order to prevent the influence of power fluctuations, work takes place in the power saturation range. This method ensures rapid response times for the measuring system, but requires correspondingly high power microwave transmitters having an output of 20 to 60 mW.

Figure 7:
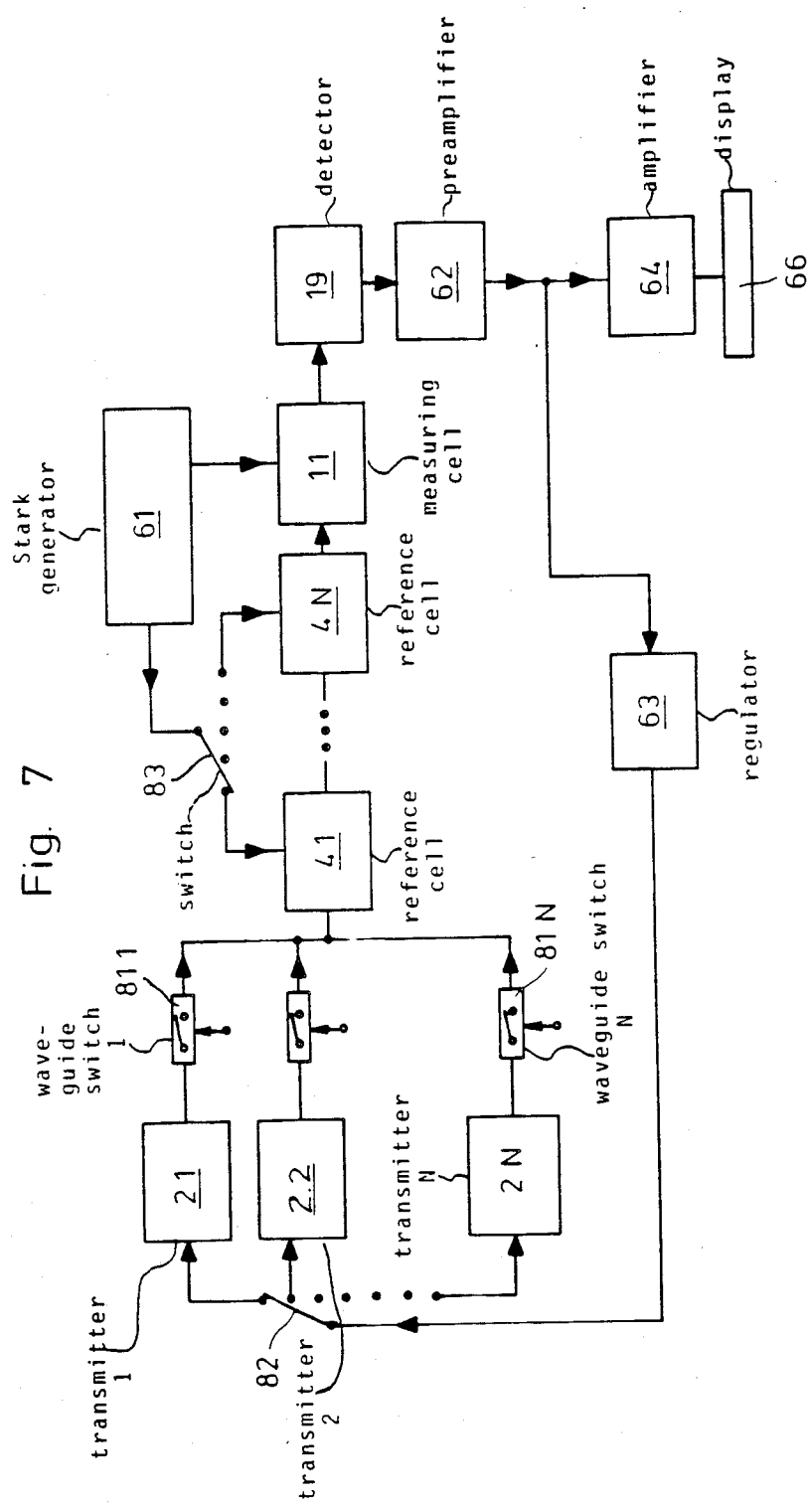
FIG. 7 is a block circuit diagram of the electronic portion of a preferred embodiment for a multicomponent gas system according to the invention.

FIG. 7 shows, as a comparison to FIG. 1, a first multicomponent gas measuring system having a plurality of reference cells 4. to 4.N connected one below the other, e.g. in a serpentine arrangement, and in series with measuring cell 11. Reference cells 4.1 to 4.N are connected via respective waveguide switches 81.1 to 81.N with tuned transmitters 2.1 to 2.N. A selected transmitter can be actuated by operating power supplied via a switch 82, while Stark voltages are applied from a Stark voltage generator 61 via a switch 83 to the respective reference cell 4.1 to 4.N.

The measurement is made in such a manner that initially the correspondingly preset Stark voltage is applied via switch 83 to reference cell 4.1 and switch 82 is used to actuate transmitter 2.1 which is then connected via waveguide switch 81.1 with the waveguide system, then a measurement is made and measurements of the gas components contained in the further reference cells are made successively thereafter. Detector 19 has an associated preamplifier whose output is connected, on the one hand, with a regulating unit 63 for microwave transmitter 2 and, on the other hand, via a lock-in amplifier 64, with a display 66 for the measurement signal.

Figure 8:
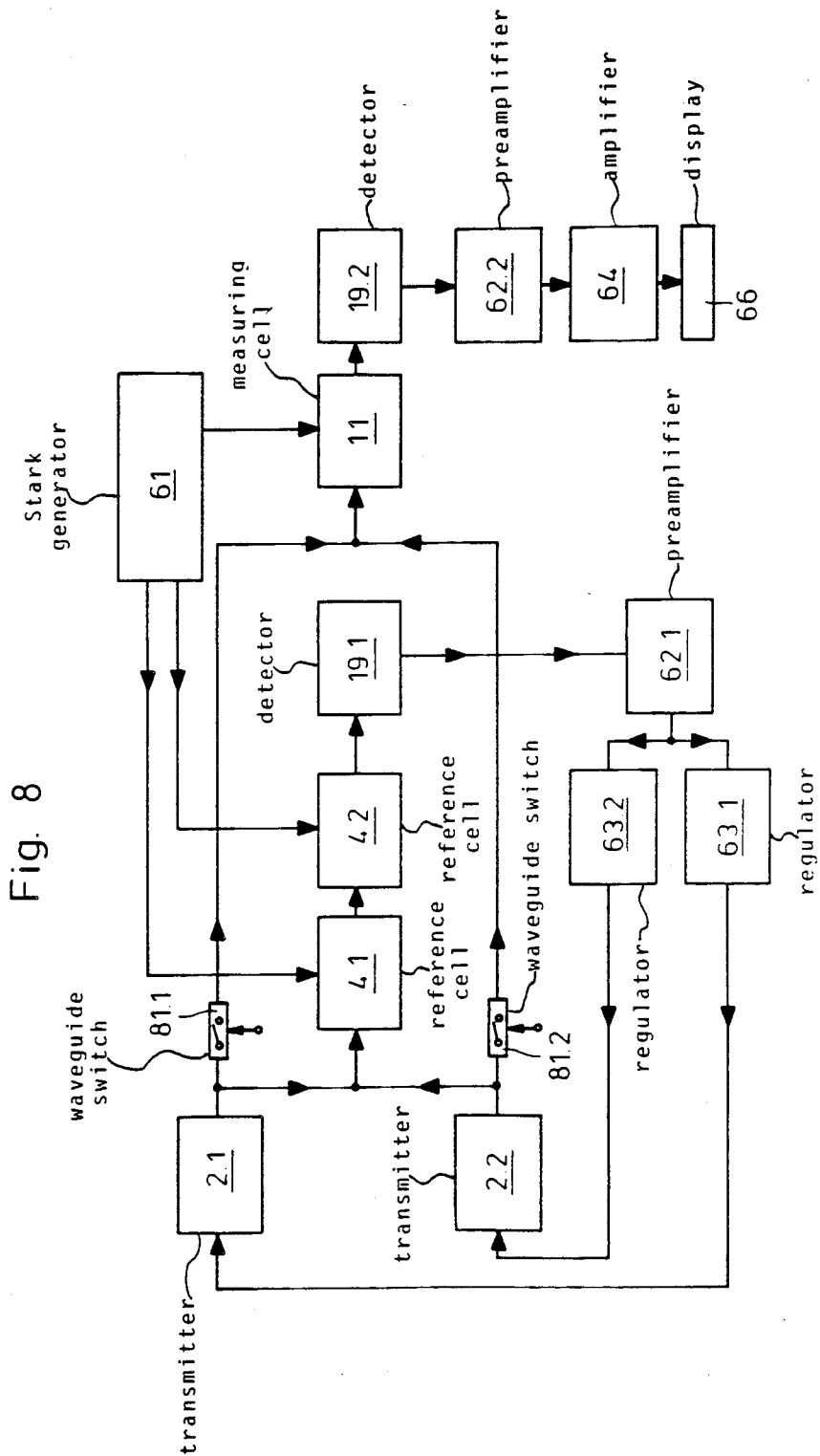
FIG. 8 is a block circuit diagram similar to that of FIG. 7 relating to a two-component system.

The delay required in the above described embodiment to achieve the frequency synchronization of the transmitters which is necessary after each switching process can be avoided in the embodiment according to FIG. 8. Here two transmitters 2.1 and 2.2 are connected with series connected reference cells 4.1 and 4.2 which are supplied with mutually phase shifted alternating Stark voltages from generator 61. Each transmitter can additionally be selectively connected via a receptive waveguide switch 81.1 or 81.2 to measuring cell 11, which must not be overloaded by connecting both transmitters to it at the same time. The frequencies of transmitters 2.1 and 2.2 are regulated by regulators 63.1 and 63.2 respectively. Both transmitters here operate continuously and are also tuned continuously so that the suitable microwave frequency is immediately available at measuring cell 11 as soon as switch 81.1 or 81.2 is thrown.

The reference cell need not in every case itself contain the pure component to be examined. If highly toxic or explosive substances are being measured, another chemical compound can also be used in its place. Such a reference compound it then selected according to the criterion that it must have an absorption line in the immediate vicinity of the selected rotational transition of the to be measured component.

By applying a direct voltage or voltages, and superposing it with the alternating Stark voltage in a reference and/or measuring cell, the S-shaped curve of the reference cell and the absorption line can be shifted with respect to one another in such a manner that the zero passage again takes place at the frequency of the line maximum.

Example: measurement of chlorine cyanide at $V=35,825.95$ MHz

The two closest absorption lines of other compounds are: toward lower frequencies $CH_3SiHDF$, $V=35,825.5$ Mhz; toward higher frequencies $CHD_2NC$ $V=35,826.44$ MHz.

The simultaneous presence of the measuring component ClCN and methyl deutero fluorosilane or dideutero methyl isocyanide in the measuring gas can be excluded and thus $V(ClCN)=35,825.95$ MHz is suitable for a quantitative determination. On the other side, the absorption lines of the partially deuterized compounds lie so closely together that the application of slight direct voltages already produces a suitable curve shape. The entire embodiment, which is held at a temperature of 50° C., is 60 cm of length, 30 cm of width and 10 cm of height.

The inner dimensions of the reference and measurement cells are preferably 0.71 cm×0.36 cm. Three parallel measurement cells of 50 cm of length, each containing a Stark electrode of 52 cm of length, are connected by ordinary waveguide bends (180°).

The length of the reference cell is 10 cm, Stark voltages are: $U_{ref}=60$ V and $U_{mes}=290$ V. Maximum of the formaldehyde absorption is at 28.97 GHz.

The invention now being fully describe, it will be apparent to one of ordinary skill in the art that many changes and modifications can be made thereto without departing from the spirit or scope of the invention as set forth herein.

The present disclosure relates to the subject matter disclosed in German Applications P 36 22 956.3 and P 36 22 957.1 of July 9th, 1986, the entire specifications of which are incorporated herein by reference.

What is claimed is:

1. In an apparatus for the analysis of gaseous media comprising a microwave transmitter; a microwave receiver; a measuring cell disposed between said transmitter and said receiver, composed of at least one Stark chamber, and having a gas inlet and a gas outlet; and at least one Stark electrode disposed in, and electrically insulated from, said chamber; the improvement comprising a plurality of mutually spaced holders, formed of insulating material, disposed within said chamber and holding and positioning said electrode in a predetermined position in said chapter.

2. Apparatus as defined in claim 1 wherein said chamber has a length dimension and an internal height dimension transverse to the length dimension, and each said holder has a height dimension in the direction of, and corresponding in magnitude to, the internal height dimension of said chamber.

3. Apparatus as defined in claim 2 wherein each said holder is made of a ceramic material.

4. Apparatus as defined in claim 3 wherein the ceramic material is a glass ceramic.

5. Apparatus as defined in claim 2 wherein said Stark electrode has two opposed edges extending parallel to the length dimension and each said holder has the basic form of a plate and is provided with a slit extending in the length dimension of said chamber, located at the middle of the height dimension of said holder, and accommodating one edge of said electrode.

6. Apparatus as defined in claim 5 including a plurality of mutually spaced said holders disposed along each said edge of said Stark electrode.

7. Apparatus as defined in claim 6 wherein each said edge is provided with a plurality of recesses and each said holder includes a part which projects from said plate and engages in a respective said recess.

8. Apparatus as defined in claim 7 wherein said insulating material is a glass ceramic.

9. Apparatus as defined in claim 2 wherein said Stark electrode has two opposed edges extending parallel to the length dimension, each edge is provided with a plurality of spaced recesses, and each said holder includes a projecting part engaging in a respective recess.

10. Apparatus as defined in claim 1 wherein said measuring cell has an internal cross section dimensioned in accordance with the frequency of the microwave signal produced by said transmitter.

11. Apparatus as defined in claim 10 wherein the internal cross-sectional dimensions of said cell are less than 10 mm×5 mm.

12. Apparatus as defiend in claim 11 wherein the internal cross-sectial dimensios of said cell are less than 8 mm×4 mm.

13. Apparatus as defined in claim 12 wherein the internal cross-sectional dimensions of said cell are approximately 7 mm×3.5 mm.

14. Apparatus as defined in claim 12 wherein the internal cross-sectional dimensions of said cell are 7.1 mm×3.6 mm.

15. Apparatus as defined in claim 1 wherein said measuring cell is composed of a plurality of Stark chambers each extending along a straight path, and a plurality of arcuate sections each interposed between successive Stark chambers, arranged so that said measuring cell extends along a meander path.

16. Apparatus as defined in claim 1 wherein: said measuring cell comprises a gas inlet member provided with said gas inlet, and a gas outlet member provided with said gas outlet, each said member having two opposed side walls and a longitudinal center axis; and said gas inlet and gas outlet are each constituted by two opposed slits each provided in a respective side wall of the associated member in line with the longitudinal axis of the associated member.

17. Apparatus as defined in claim 16 wherein each said slit has a length of about 10 mm in the direction of the longitudinal axis of the associated member, and width of about 0.5 mm.

18. Apparatus as defined in claim 16 wherein each said member further comprises: a gas flow chamber extending around said side walls of said member and enclosing said slits; and a gas conduit connected to said gas flow chamber.

19. Apparatus as defined in claim 1 further comprising: a gas inlet valve having an inlet part, an outlet part, a main flow path for a gas to be measured extending between said inlet and outlet parts, and means defining a branch flow path extending from said main flow path at an angle to the direction of said main flow path; and wherein said branch flow path is connected to said gas inlet of said measuring cell.

20. Apparatus as defined in claim 19 wherein the angle is about 90°.

21. Apparatus as defined in claim 19 wherein said gas inlet valve is a mechanically operated valve.

22. Apparatus as defined in claim 19 wherein said gas inlet valve is an electrically operated valve.

23. Apparatus as defined in claim 1 further comprising a reference cell composed of at least one Stark chamber and having a gas inlet and a gas outlet.

24. Apparatus as defined in claim 23 further comprising: a permeation system connected for supplying the component in pure form to said reference cell, said permeation system including a source of the component, a temperature regulating device for regulating the temperature of said source, and a pressure regulating device connected for controlling said temperature regulating device; and a pressure sensor connected for sensing the gas pressure in said reference cell and for connecting said pressure regulating device.

25. Apparatus as defined in claim 23 further comprising a capillary member connected downstream of said reference cell outlet for effecting flow stabilization.

26. Apparatus as defined in claim 23 further comprising gas filter means connected downstream of said reference cell outlet.

27. Apparatus as defined in claim 23 further comprising a common thermostat system for said measuring and reference cells.

28. Apparatus as defined in claim 1 wherein said insulating material is a glass ceramic.

* * * * *